United States Patent [19] [11] 4,257,939

Sakakibara [45] Mar. 24, 1981

[54] PEPTIDE DERIVATIVE
[75] Inventor: Shumpei Sakakibara, Suita, Japan
[73] Assignee: Ajinomoto Co., Inc., Tokyo, Japan
[21] Appl. No.: 87,922
[22] Filed: Oct. 25, 1979
[51] Int. Cl.$^3$ ............................................. C07C 103/52
[52] U.S. Cl. ............................................. 260/112.5 R
[58] Field of Search ................................. 260/112.5 R
[56] References Cited
U.S. PATENT DOCUMENTS

| | | | |
|---|---|---|---|
| 3,884,896 | 5/1975 | Blomback et al. | 260/112.5 R |
| 4,028,318 | 6/1977 | Aurell et al. | 260/112.5 R |

*Primary Examiner*—Delbert R. Phillips
*Attorney, Agent, or Firm*—Oblon, Fisher, Spivak, McClelland & Maier

[57] ABSTRACT

A peptide derivative useful as substrates for determining enzymatic activities have the following formula

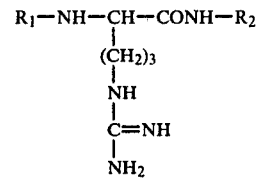

wherein $R_1$ is a group selected from the group consisting of seryl, phenylalanyl-seryl, threonyl and leucyl-threonyl groups, and $R_2$ is

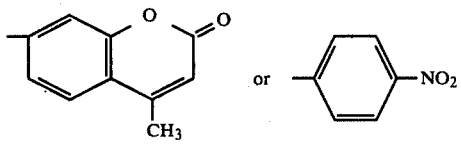

6 Claims, 1 Drawing Figure

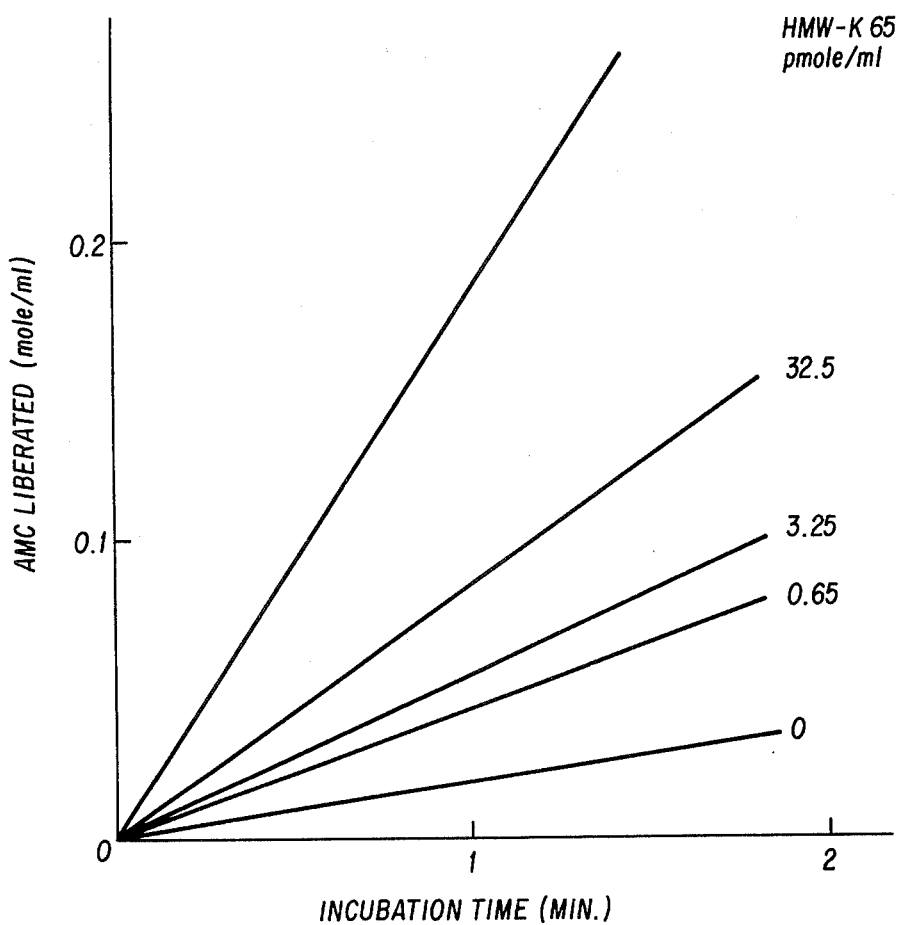

PEPTIDE DERIVATIVE

The present invention relates to a novel peptide derivative useful as substrate for measuring the activity of specific enzymes, or an intermediate product thereof.

As a result of perseverant efforts towards obtaining a substrate whereby activity of specific enzymes can be measured in a simple and highly sensitive way, inventor has succeeded in synthesizing a peptide derivative shown by a general formula

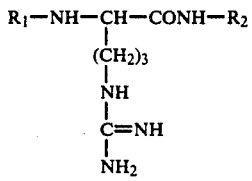

and discovered that the novel peptide derivative may be used as a substrate, or its intermediate product, for an enzyme such as Factor $XI_a$, the activity of which can be measured in a simple and highly sensitive way. In the formula, $R_1$ designates seryl, phenylalanyl-seryl, threonyl or leucyl-threonyl group, and $R_2$ designates

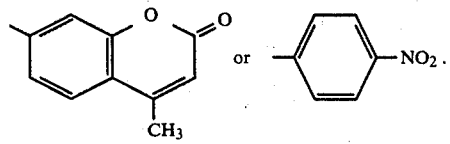

In the peptide derivative of the above general formula, the terminal $N^\alpha$-amino group may be protected by customarily employed protecting groups for the $N^\alpha$-amino group of peptides such as acyl groups such as acetyl or benzoyl, carbobenzoxy group, tert-alkyloxycarbonyl group, tosyl group or glutaryl group, while the hydroxyl group may be protected by protecting group which is used in the conventional method for synthesizing peptide, such as alkyl group and benzyl group.

The guanidino group of arginine which is found in the peptide derivative may be protected by N-guanidino-protecting group which is used in the conventional method for synthesizing peptides, such as the nitro group, the tosyl group and the p-methoxybenzenesulfonyl group, and by adding a proton such as by reacting it with an acid.

The above-mentioned peptide derivative may be in the form of an acid addition salt of, for example, acetic acid or hydrochloric acid or in the form of hydrate.

The above-mentioned peptide derivative is (seryl-arginyl)-4-methylcoumaryl-7-amide or seryl-arginine-p-nitroanilide if $R_1$ is seryl group; (phenylalanyl-seryl-arginyl)-4-methylcoumaryl-7-amide or phenylalanyl-seryl-arginine-p-nitroanilide if $R_1$ is phenylalanyl-seryl group; (lysyl-arginyl)-4-methylcoumaryl-7-amide or lysyl-arginine-P-nitroanilide if $R_1$ is lysyl group; (leucyl-threonyl-arginyl)-4-methylcoumaryl-7-amide or leucyl-threonyl-arginine-P-nitroanilide if $R_1$ is leucyl-threonyl group.

A p-nitroanilide derivative in the peptide derivative of the present invention can be synthesized in, for example, a following way.

An ester of $N^\alpha$-protective-serine is converted into hydrazide derivative thereof by conventional method and is reacted with p-nitroanilide derivative of arginine to produce seryl-arginine-p-nitroanilide derivative.

An ester of $N^\alpha$-protective-phenylalanyl-serine is converted into hydrazide derivative thereof by conventional method and is reacted with p-nitroanilide derivative of arginine to produce phenylalanyl-seryl-arginine-p-nitroanilide derivative.

An ester of $N^\alpha$-protective-threonine is converted into hydrazide derivative thereof by conventional method and is reacted with p-nitroanilide derivative of arginine to produce threonyl-arginine-p-nitroanilide derivative.

An ester of $N^\alpha$-protective-leucyl-threonine is converted into hydrazide derivative thereof by conventional method, and is reacted with p-nitroanilide derivative of arginine to produce leucyl-threonyl-arginine-p-nitroanilide derivative.

A 4-methylcoumaryl-7-amide derivative in the peptide derivative of the present invention can be synthesized in, for example, in a following way.

7-amino-4-methylcoumarin and arginine, amino group and guanidino group of which are protected, are reacted together in the presence of a condensing agent such as dicyclohexylcarbodiimide (DCCD) conventionally employed for peptide synthesis. Next, the protecting groups for the amino group and the guanidino group are removed in a manner as conventionally used in peptide synthesis for providing arginyl-4-methylcoumaryl-7-amide.

The peptide derivative of the present invention can be prepared by the use of the thus obtained arginyl-4-methylcoumaryl-7-amide as a starting material and by using a conventional manner employed in peptide synthesis. For example, by reacting serine of which the amino group and the hydroxyl group are protected, with the above-mentioned the 4-methylcoumaryl-7-amide derivative in which $N^\alpha$-amino group is not protected in the presence of said condensing agent, or by reacting an active ester of serine as mentioned before with the above-mentioned 4-methylcoumaryl-7-amide derivative, and then removing the protecting groups, ($N^\alpha$-seryl-arginyl)-4-methylcoumaryl-7-amide is obtained. Further, by reacting ($N^\alpha$-nonprotective-seryl-$N^G$-protective-arginyl)-4-methylcoumaryl-7-amide with an active ester of phenylalanine of which amino group is protected, and then removing the protecting groups in the same manner as above, (Phenylalanyl-seryl-arginyl)-4-methylcoumaryl-7-amide is obtained.

By reacting ($N^\alpha$-nonprotective-$N^G$-protective-arginyl)-4-methylcoumaryl-7-amide with an active ester of threonine of which amino group is protected, and then removing the protecting groups in the same manner as above, (threonyl-arginyl)-4-methylcoumaryl-7-amide is obtained.

By reacting $N^\alpha$-nonprotective-threonyl-arginyl)-4-methylcoumaryl-7-amide with an active ester of leucine of which amino group is protected, and then removing the protecting groups in the same manner as above, (leucyl-threonyl-arginyl)-4-methylcoumaryl-7-amide is obtained.

The condensation reaction for the synthesis of the peptide derivative of the present invention should preferably be conducted in a suitable solvent such as dimethylformamide (DMF), dimethylsulfoxide, water or mixtures thereof. The carboxyl component to be reacted with an amino component should preferably be employed in the form of an active ester which may preferably be N-hydroxysuccinimide ester or p-nitrophenylester. While the reaction using this active ester proceeds sufficiently at room temperature, it may also be promoted by heating as the occasion may demand.

After completion of reaction, the reaction mixture is concentrated and dried to a solid substance and the residue is refined by column chromatography and freeze-dried.

If the resulting compound has protective groups for an amino or carboxylic group, these protecting groups may be removed by employing a conventional removing process for the protective groups. For example, carbobenzoxy groups or benzyl ester can be removed by hydrogenation in alcohol or similar solvent, while tert-butyloxycarbonyl group can be removed by reacting the same with toluensulfonic acid for about 90 minutes in acetic acid or other solvents.

The peptide derivative of the present invention in an isolated form may be converted into an acid salt, or the peptide derivative in the form of an acid salt may be converted into an isolated form, as the occasion may demand. Examples of such acid salts are inorganic acid salts such as hydrochloride, sulfate, nitrate or phosphate and organic acid salts such as acetate, oxalate, tartarate, succinate, citrate or toluensulfonate.

The peptide derivative thus obtained were identified by elementary analysis, amino acid analysis, and UV absorption spectrum.

As the peptide derivative of the present invention may be hydrolyzed by enzymes such as Factor $XI_a$ and the like, the peptide derivative is highly suitable as synthetic substrate for these specific enzymes.

The amino acid comprised in the peptide derivative of the present invention may be in the L- or D-form, however, the L-form is more preferred.

The present invention is illustrated in more detail by the following Examples.

EXAMPLE 1

17.2 g of L-serine methyl ester hydrochloric acid salt were dissolved in 200 ml of dichloromethane and to this solution 15.4 ml of triethylamine was added. To this mixture an homogeneous solution of 36.2 g of tert-butyloxycarbonyl-L-phenylalanine-N-hydroxysuccinimide ester in 200 ml of tetrahydrofuran (THF) was added. The mixture was stirred for 15 hours at room temperature and then solvent was removed under reduced pressure from the reaction mixture. The residue was dissolved in 300 ml of ethyl acetate and the solution was shaken with 100 ml of 0.5 N hydrochloric acid.

An organic layer was washed with 100 ml of 5% aqueous solution of sodium bicarbonate and with 100 ml of water, and dried over magnesium sulfate. The drying agent was removed by filtration and thus obtained organic layer was concentrated under reduced pressure to obtain a solid substance. To the residual substance 500 ml of n-hexane were added to produce a gel-like solid substance. The solid substance was obtained by filtration and washed with n-hexane and dried to give tert-butyloxycarbonyl-L-phenylalanyl-L-serine methyl ester.

Yield: 36 g (98%), melting point: 90~93° C., specific rotation $[\alpha]_D^{25} = -0.18°$ (C=2.75, DMF).

Elemental analysis: Calculated for $C_{18}H_{26}N_2O_6 \cdot \frac{1}{2}H_2O$: C 58.28%, H 7.20%, N 7.55%. Found: C 58.46%, H 7.30%, N 7.43%.

18.3 g of tert-butyloxycarbonyl-L-phenylalanyl-L-serine methyl ester were dissolved in 50 ml of methyl alcohol, and to this solution 7.5 ml of 80% hydrazine mono hydrate were added. The mixture was stirred for 15 hours at room temperature and then the reaction mixture was concentrated under reduced pressure to give a solid substance. The solid substance was allowed to re-crystallization with ethyl alcohol and thereby tert-butyloxycarbonyl-L-phenylalanyl-L-serine hydrazide was obtained.

Yield: 12.8 g (70%), melting point: 176~177° C. (dec.), specific rotation $[\alpha]_D^{25} = -3.33°$ (C=2.52, DMF).

Elemental analysis: Calculated for $C_{17}H_{26}N_4O_5$:C 55.72%, H 7.15%, N 15.29%. Found: C 55.83%, H 7.17%, N 15.28%.

2.75 g of tert-butyloxycarbonyl-L-phenylalanyl-L-serine hydrazide were dissolved in 30 ml of DMF and to this solution 2.4 ml of 6.3 N hydrogen chloride dioxane solution were obtained. To this mixture 1.17 g of iso-amyl nitrite were added while cooling at −30° C. and thus obtained mixture was stirred for 15 minutes at −15° C., and then to this mixture 2.1 ml of triethylamine were added.

1.84 g of L-arginine-p-nitroanilide hydrochloric acid salt were dissolved in 20 ml of DMF and to this solution 0.7 ml of triethylamine were added.

The both solutions as obtained above were mixed together at less than −10° C. and thus obtained mixture was stirred for 20 hours at −7° C.

The reaction mixture was concentrated under reduced pressure to give a solid substance and the substance wa dissolved in 200 ml of ethyl acetate and 200 ml of aqueous solution saturated with sodium chloride and then shaken. An organic layer was shaken with 200 ml of aqueous solution saturated with sodium chloride, once more and dried over magnesium sulfate. The solvent was removed by distillation under reduced pressure, and the remaining substance was purified with silica gel chromatography (column size: 3×20 cm, solvent system, chloroform: methyl alcohol: acetic acid=20:2:1 and 20:40:1). The main fractions were collected and subjected to concentration to a solid substance. The substance was dissolved in 100 ml of acetic acid and freeze-dried to give tert-butyloxycarbonyl-L-phenylalanyl-L-seryl-L-arginine-p-nitroanilide hydrochloric acid salt.

Yield: 2.35 g (71%), melting point: 150° C. (dec.), specific rotation $[\alpha]_D^{25} = -23.1°$ (C=0.64, DMF).

Elemental analysis: Calculated for $C_{29}H_{40}N_8O_8 \cdot HCl \cdot CH_3COOH$: C 51.34%, H 6.25%, N 15.45%. Found: C 51.40%, H 6.41%, N 14.96%.

EXAMPLE 2

250 ml of ethyl alcohol were added to 13.1 g of L-threonine, and into thus obtained solution hydrogen chloride gas was brown, and thereby the solution was saturated with hydrogen chloride. This mixture was stood for 20 hours at room temperature and then concentrated under reduced pressure to a solid substance. To the substance 200 ml of dichloromethane and 15.4 ml of triethylamine were added. To this solution a homogeneous solution of 32.8 g of tert-butyloxycarbonyl-L-leucine-N-hydroxysuccinimide ester in 200 ml of THF were added, and thus obtained mixture was stirred for 15 hours at room temperature and concentrated under reduced pressure to a solid substance. The substance was dissolved in 300 ml of ethyl acetate and 100 ml of ½ N hydrochloric acid and then shaken. An organic layer was then washed with 100 ml of a 5% aqueous solution of sodium bicarbonate, and then with 100 ml of water. Thus obtained organic layer was dried over magnesium sulfate. The drying agent was removed by filtration and thus obtained residue was concentrated under reduced pressure to a solid substance. To the remaining substance 50 ml of ethyl acetate and 400 ml of n-hexane were added. The crystallization was induced by rubbing with glass rode while cooling. The produced crystals were obtained by filtration and then washed with n-hexane to give tert-butyloxycarbonyl-L-leucyl-L-threonine ethyl ester.

Yield: 34 g (94%), melting point: 67°~70° C., specific rotation $[\alpha]_D^{25} = -19.3°$ (C=1.95, DMF).

Elemental analysis: Calculated for $C_{17}H_{32}N_2O_6$: C 56.64%, H 8.95%, N 7.77%. Found: C 57.16%, H 9.40%, N 7.40%.

18 g of tert-butyloxycarbonyl-L-leucyl-L-threonine ethyl ester was dissolved in 50 ml of methyl alcohol, and then 7.5 ml of 80% hydrazine monohydrate was added thereto. Thus obtained mixture was stirred overnight at room temperature, and then was concentrated under reduced pressure to a solid substance.

The substance was dissolved in 50 ml of ethyl alcohol and then a gel like solid substance was produced by addition of ethyl ether thereto. The substance was obtained by filtration and then washed with ethyl ether to give tert-butyloxycarbonyl-L-leucyl-L-threonine hydrazide.

Yield: 15 g (87%), melting point: 146°~148° C., specific rotation $[\alpha]_D^{25} = -20.8°$ (C=1.46, DMF).

Elemental analysis: Calculated for $C_{15}H_{30}N_4O_5$: C 52.00%, H 8.73%, N 16.18%. Found: C 52.29%, H 8.87%, N 16.20%.

2.60 g of tert-butyloxycarbonyl-L-leucyl-L-threonine hydrazide were dissolved in 30 ml of DMF, and then 2.4 ml of 6.3 N hydrogen chloride dioxane solution were added thereto, and then 1.17 g of isoamyl nitrite were added thereto at −30° C. Thus obtained mixture was stirred for 15 minutes at −15° C. and then 2.1 ml of triethylamine were added at −70° C. thereto.

On the other hand, 1.84 g of L-arginine-P-nitroanilide 2 hydrochloric acid salt was dissolved in 20 ml of DMF and then 0.7 ml of triethylamine were added thereto.

The both solutions as obtained above were mixed together at −10° C. or less than −10° C., and then the mixture was stirred for 45 hours at 0° C.

The reaction mixture was concentrated under reduced pressure to a solid substance and then the residual substance was dissolved in 200 ml of ethyl acetate and 200 ml of aqueous solution saturated with sodium chloride and then the mixture was shaken. An organic layer was shaken with 200 ml of aqueous solution saturated with sodium chloride once more, and then dried over magnesium sulfate. The solvent was removed by filtration under reduced pressure and the remaining substance was subjected to silica gel column chromatography (column size: 3×20 cm; solvent system, chloroform: methyl alcohol: acetic acid=20:2:1 and 20:4:1) for refining. The main fractions were collected, mixed together and concentrated to a solid substance. The residual substance was dissolved in 100 ml of acetic acid and freeze-dried to give tert-butyloxycarbonyl-L-leucyl-L-threonyl-L-arginine-p-nitroanilide hydrochloric acid salt.

Yield: 1.82 g (56%), melting point: 152° C. (dec.), specific rotation $[\alpha]_D^{25} = -31.6°$ (C=0.82, DMF).

Elemental analysis: Calculated for $C_{27}H_{44}N_8O_8 \cdot HCl \cdot CH_3COOH$: C 49.39%, H 7.00%, N 15.89%. Found: C 49.67%, H 7.30%, N 15.24%.

EXAMPLE 3

2.75 g of tert-butyloxycarbonyl-L-phenylalanyl-L-serine hydrazide were dissolved in 30 ml of DMF, and then 2.4 ml of 6.3 N hydrogen chloride dioxane solution were added thereto, and then 1.17 g of isoamyl nitrite were added at −30° C. thereto. Thus obtained mixture was stirred for 15 minutes at −15° C. and then 2.1 ml of triethylamine were added at −70° C. thereto.

On the other hand, 2.51 g of (carbobenzoxy-L-argininyl)-4-methylcoumaryl-7-amide hydrochloric acid salt were dissolved in 50 ml of methyl alcohol, 10 ml of acetic acid and 10 ml of water, and then 250 g of 5% polladium-carbon catalyst were added thereto. Thus obtained mixture was stirred for 3 hours at room temperature and atmospheric pressure under circulation of hydrogen for catalytic reduction. The catalyst was then removed and the filtrate was concentrated under reduced pressure to a solid substance. The remaining substance was dissolved in 20 ml of DMF, 15 ml of water and 5 ml of acetic acid.

The both solutions as obtained above, were mixed together at not more than −10° C., and then PH value of thus obtained solution was adjusted to 7 by addition of triethylamine. Thus obtained mixture was stirred for 20 hours at −7° C., and then concentrated under reduced pressure to a solid substance. The remaining substance was dissolved in 200 ml of ethyl acetate, 50 ml of methylalcohol and 200 ml of aqueous solution saturated with sodium chloride and was shaken.

An organic layer was shaken with 100 ml of aqueous solution with saturated sodium chloride once more and then the organic layer was separated and concentrated to a solid substance.

The remaining substance was subjected to silica gel chromatography (column size: 3×20 cm; solvent system, chloroform: methyl alcohol: acetic acid=20:2:1 and 20:4:1) for refining and the main fractions were collected, mixed together and concentrated to a solid substance. The remaining substance was dissolved in 100 ml of acetic acid and freeze-dried to give (tert-butyloxycarbonyl-L-phenylalanyl-L-seryl-L-arginyl)-4-methylcoumaryl-7-amide.

Yield: 2.2 g (63%), melting point: 155° C. (dec.), specific rotation $[\alpha]_D^{25} = -26.2°$ (C=0.61, DMF).

Elemental analysis: Calculated for $C_{33}H_{43}N_7O_8 \cdot HCl \cdot 2CH_3COOH$: C 54.04%, H 6.37%, N 11.93%. Found: C 53.09%, H 6.44%, N 11.76%.

EXAMPLE 4

2.60 g of tert-butyloxycarbonyl-L-leucyl-L-threonine hydrazide was dissolved in 30 ml of DMF, and then 2.4 ml of 6.3 N hydrogen chloride dioxane solution were added thereto and then 1.17 g of isoamylnitrite were added at −30° C. Thus obtained mixture was stirred for 15 minutes at −15° C., and then 2.1 ml of triethylamine were added at −70° C. thereto.

On the other hand, 2.51 g of (carbobenzoxy-L-arginyl)-4-methylcoumaryl-7-amide were dissolved in 50 ml of ethyl alcohol, 10 ml of acetic acid and 10 ml of water, and then 250 mg of a 5% palladium-carbon catalyst were added thereto. The resulting mixture was stirred for 3 hours at room temperature and atmospheric pressure under circulation of hydrogen for catalytic reduction. The catalyst was then removed and the filtrate was concentrated under reduced pressure to a solid substance. The remaining substance was dissolved in 20 ml of DMF, 15 ml of water and 5 ml of acetic acid.

The both solution as obtained above, was mixed together at $-10°$ C. or less than $-10°$ C. and PH value of thus obtained mixture was adjusted to 7 by addition to triethylamine thereto. Thus obtained mixture was stirred for 45 hours at $0°$ C., and then concentrated under reduced pressure to a solid substance. The remaining substance was dissolved in 200 ml of ethyl acetate, 50 ml of methyl alcohol and 200 ml of aqueous solution saturated with sodium chloride and thus obtained mixture was shaken. An organic layer was shaken with 100 ml of aqueous solution saturated with sodium chloride once more and a organic layer was concentrated to a solid substance. The remaining substance was subjected to silica gel chromatography (column size:$3\times20$ cm, solvent system: chloroform: methyl alcohol: acetic acid=20:2:1 and 20:4:1) for refining. The main fractions were collected and mixed together and concentrated to a solid substance. The remaining substance was dissolved in 100 ml of acetic acid and freeze-dried to give (tert-butyloxycarbonyl-L-leucyl-L-threonyl-L-arginyl)-4-methylcoumaryl-7-amide hydrochloric acid salt.

Yield: 1.90 g (56%), melting point: 160° C. (dec.), specific rotation $[\alpha]_D^{25}=-40.0°$ (C=0.35, DMF).

Elemental analysis: Calculated for $C_{31}H_{47}N_7O_8 \cdot HCl \cdot 2CH_3COOH$: C 52.39%, H 7.04%, N 12.22%. Found: C 51.96%, H 7.19%, N 12.44%.

EXAMPLE 5

5.02 g of (carbobenzoxy-L-arginyl)-4-methylcoumaryl-7-amide hydrochloric acid salt were dissolved in 20 ml of acetic acid, 100 ml of methyl alcohol and 20 ml of water, and then 500 mg of 5% palladium-carbon catalyst were added thereto. The resulting mixture was stirred for 3 hours at room temperature and atmospheric pressure under circulation of hydrogen for catalytic reduction. The catalyst was then removed and the filtrate was concentrated under reduced pressure to a solid substance.

The remaining substance was dissolved in 20 ml of DMF and 2 ml of water, and then 4.7 g of tert-butyloxycarbonyl-O-benzyl-L-serine-N-hydroxysuccinimide ester were added thereto. Thus obtained mixture was stirred. The solvent was removed by distillation under reduced pressure. The remaining substance was subjected to a silica gel chromatography (column size: $4\times20$ cm; solvent system, chloroform: methyl alcohol: acetic acid=85:15:5) for refining and the main fractions were collected and mixed together.

To the remaining substance ether was added to give powder. The powder was obtained by filtration and thereby (tert-butyloxycarbonyl-O-benzyl-L-seryl-L-arginyl)-4-methylcoumaryl-7-amide hydrochloric acid salt were obtained.

Yield: 2.6 g (40%), melting point: 150° C. (dec.), specific rotation $[\alpha]_D^{25}=-20.5°$ (C=0.43, DMF).

Elemental analysis: Calculated for $C_{31}H_{40}O_7N_6 \cdot HCl \cdot CH_3COOH$: C 56.20%, H 6.43%, N 11.92%. Found: C 55.71%, H 6.29%, N 12.00%.

EXAMPLE 6

5.02 g of (carbobenzoxy-L-arginyl)-4-methylcoumaryl-7-amide was dissolved in 20 ml of acetic acid, 100 ml of methyl alcohol and 20 ml of water, and then 500 mg of a 5%-palladium-carbon catalyst were added thereto. The resulting mixture was stirred for 3 hours at room temperature and atmospheric pressure under circulation of hydrogen for catalytic reduction.

The catalyst was then removed and from the filtrate the solvent was removed by distillation under reduced pressure. Thus obtained residue was dissolved in 20 ml of DMF and 2 ml of water, and then 4.9 g of tert-butyloxycarbonyl-O-benzyl-L-threonine-N-hydroxysuccinimide ester were added thereto. Thus obtained mixture was stirred for 20 hours and then concentrated under reduced pressure to a solid substance.

The remaining substance was subjected to silica gel chromatography (column size: $4\times20$ cm; solvent system, chloroform: methyl alcohol: acetic acid=95:5:3 and 85:15:5) for refining and the main fractions were collected and subjected to concentration to a solid substance. The substance was dissolved in 20 ml of hot acetic acid and then allowed to recrystallization to give (t-butyloxycarbonyl-O-benzyl-L-threonyl-L-arginyl)-4-methylcoumaryl-7-amide hydrochloric acid salt.

Yield: 3.1 g, melting point: 218° C. (dec.) specific rotation $[\alpha]_D^{25}=-24.4°$ (C=0.71, DMF).

Elemental analysis: Calculated for $C_{32}H_{42}O_7N_6 \cdot HCl \cdot CH_3COOH$: C 56.77%, H 6.59%, N 11.69%. Found: C 57.33%, H 6.56%, N 11.74%.

EXAMPLE 7

1.29 g of (tert-butyloxycarbonyl-O-benzyl-L-seryl-L-arginyl)-4-methylcoumaryl-7-amide hydrochloric acid salt, 4 ml of acetic acid and 450 mg of p-toluene sulfonic acid mono hydrate were mixed together and stirred for 3 hours at 20° C. Powders were produced by addition of 100 ml of ether and obtained by filtration. The powders were dissolved in 10 ml of DMF and the PH value was adjusted to 7 by addition of triethylamine thereto. To thus obtained mixture 1.09 g of tert-butyloxycarbonyl-L-phenylalanine-N-hydroxysuccinimide ester were added and thus obtained mixture was stirred for 20 hours at room temperature and then concentrated to a solid substance. The remaining substance was dissolved in 50 ml of ethyl acetate and the solution was washed with 50 ml of 0.5 N hydrochloric acid and then 50 ml of water and dried over magnesium sulfate, and then concentrated to a solid substrate. The remaining substance was subjected to silica gel chromatography (column size: $2\times15$ cm; solvent system, chloroform: methyl alcohol: acetic acid=95:5:3 and 95:30:3) for refining and the main fractions were collected and subjected to concentration to a solid substance.

The remaining substance was dissolved in 50 ml of acetic acid and freeze-dried to give (tert-butyloxycarbonyl-L-phenylalanyl-O-benzyl-L-seryl-arginyl)-4-methylcoumaryl-7-amide hydrochloric acid salt.

Yield: 1.21 g (76%), melting point: 150° C. (dec.), specific rotation $[\alpha]_D^{25}=-10.6°$ (C=0.52, DMF).

Elemental analysis: Calculated for $C_{40}H_{49}O_8N_7 \cdot HCl \cdot CH_3COOH$: C 59.18%, H 6.39%, N 11.51%. Found: C 59.51%, H 6.10%, N 10.83%.

Activities of Factor XI were determined as follows:

To Factor XI ($A_{280}=1.72$) and Factor XII$_a$ ($A_{280}=0.028$), 5 μl of HMW kininogen (HMW-K; 65, 32.5, 3.25, 0.65 and 0 P mole/ml) were mixed respectively, and then 10 μl of Kaolin (1.25 mg/ml) were added respectively thereto. Thus obtained mixtures were incubated at 37° C. for 30 minutes and then 5 μl of (tert-butyl-oxycarbonyl-L-phenylalanyl-L-seryl-L-arginyl)-4-methylcoumaryl-7-amide (=Boc-Phe-Ser-Arg-MCA; 10 mM) were added thereto. 7-amino-4- methylcoumarin (=AMC) as liberated in the enzyme reaction by using a Hitachi spectrofluorophotometer.

Now, Factor XII$_a$ was used as the form of solution comprising 0.1 M sodium chloride and 0.02 M tris-buffer (PH 8.0) containing Bovine serum albumin (0.1 mg/ml).

Results were listed in FIG. 1. As is evident from the FIG. 1., activity of Factor XI$_a$ is in proportion to volumes of High Molecular Weight-K, and therefore, volumes of Factor XI$_a$ can be determined by using Boc-Phe-Ser-Arg-MCA.

In table 1, relative reaction rates of Factor IX$_a$, Factor XI$_a$ and Factor XII$_a$ to 7-amino-4-methylcoumarin derivative of the present invention were shown. As is evident from the table, Boc-Phe-Ser-Arg-MCA is hydrolyzed partially by Factor IX$_a$ and Factor XII and however, it is impossible that this partial hydrolyzation have a bad influence upon determination of Factor XII since the Factor IX don't scarcely contaminate fraction of Factor XI.

The Factor XII can be almost neglected since ability of hydrolyzation to Boc-Phe-Ser-Arg-MCA is about 1/5 even if Factor XII contaminate.

As is evident from the table 1, (tert-butyl-oxycarbonyl-L-leucyl-L-threonyl-L-arginyl)-4-methylcoumaryl-7-amide (=Boc-Leu-Thr-Arg-MCA) is much more specific than Boc-Phe-Ser-Arg-MCA as substrate for Factor XI$_a$.

TABLE 1

| Substrate | Relative Reaction Rate | | |
|---|---|---|---|
| | Factor IX$_a$ | Factor XI$_a$ | Factor XII$_a$ |
| Boc—Phe—Ser—Arg—MCA | 29 | 100 | 14 |
| Boc—Leu—Thr—Arg—MCA | indetectable | 182 | 10 |

It was confirmed that the other peptide derivatives of the present invention are good substrate for Factor XI by similar experiments as above.

What is claimed is:

1. A peptide derivative having the formula

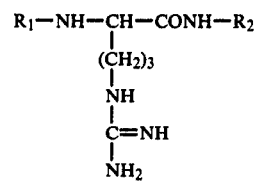

wherein R$_1$ is a group selected from the group consisting of seryl, phenylalanyl-seryl, threonyl and leucyl-threonyl groups, and R$_2$ is

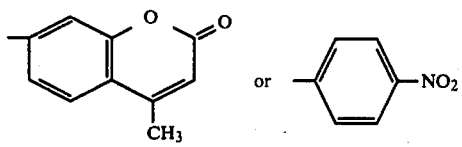

2. The peptide derivative of claim 1 wherein the peptide derivative is in the form of an acid addition salt.
3. The peptide derivative of claim 1 wherein the terminal N$^\alpha$-amino group is protected.
4. The peptide derivative of claim 1 wherein the hydroxyl group is protected.
5. The peptide derivative of claim 3 wherein the protecting group for the terminal N$^\alpha$-amino group is a group selected from the group consisting of acyl, carbobenzoxy, tert-alkyloxycarbonyl, tosyl, and glutaryl groups.
6. The peptide derivative of claim 1 wherein the guanidino group of arginine which is found in the peptide derivative is protected by N-guanidino-protecting group.

* * * * *

UNITED STATES PATENT AND TRADEMARK OFFICE
CERTIFICATE OF CORRECTION

PATENT NO. : 4,257,939
DATED : March 24, 1981
INVENTOR(S) : SHUMPEI SAKAKIBARA

It is certified that error appears in the above—identified patent and that said Letters Patent is hereby corrected as shown below:

Please insert the Priority Data to read as follows:

[30]--Foreign Application Priority Data

November 2, 1978 [JP] Japan.................135634

Signed and Sealed this

Second Day of June 1981

[SEAL]

Attest:

RENE D. TEGTMEYER

*Attesting Officer*     *Acting Commissioner of Patents and Trademarks*